United States Patent
Hishida et al.

(10) Patent No.: US 9,811,898 B2
(45) Date of Patent: Nov. 7, 2017

(54) IMAGE ANALYZING APPARATUS AND PROGRAM

(71) Applicants: IHI CORPORATION, Koto-ku (JP); The University of Tokyo, Bunkyo-ku (JP)

(72) Inventors: Hiroyuki Hishida, Koto-ku (JP); Koichi Inagaki, Koto-ku (JP); Takeshi Nakamura, Koto-ku (JP); Takashi Michikawa, Bunkyo-ku (JP); Hiromasa Suzuki, Bunkyo-ku (JP)

(73) Assignees: IHI CORPORATION, Koto-ku (JP); THE UNIVERSITY OF TOKYO, Bunkyo-ku (JP)

( * ) Notice: Subject to any disclaimer, the term of this patent is extended or adjusted under 35 U.S.C. 154(b) by 0 days.

(21) Appl. No.: 15/025,799

(22) PCT Filed: Sep. 29, 2014

(86) PCT No.: PCT/JP2014/075945
§ 371 (c)(1),
(2) Date: Mar. 29, 2016

(87) PCT Pub. No.: WO2015/046530
PCT Pub. Date: Apr. 2, 2015

(65) Prior Publication Data
US 2016/0232653 A1    Aug. 11, 2016

(30) Foreign Application Priority Data
Sep. 30, 2013  (JP) ................................ 2013-204596

(51) Int. Cl.
*G06K 9/00*    (2006.01)
*G06T 7/00*    (2017.01)
(Continued)

(52) U.S. Cl.
CPC .......... *G06T 7/001* (2013.01); *G01N 21/8851* (2013.01); *G01N 23/04* (2013.01);
(Continued)

(58) Field of Classification Search
USPC ........................................................ 382/141
See application file for complete search history.

(56) References Cited

U.S. PATENT DOCUMENTS

2010/0278440 A1    11/2010  Dragovich et al.
2012/0330447 A1*   12/2012  Gerlach ................ G01B 11/24
                                                700/95
(Continued)

FOREIGN PATENT DOCUMENTS

EP    2 246 820 A1    11/2010
JP    2009-198463 A    9/2009
JP    2010-261933 A    11/2010

OTHER PUBLICATIONS

International Search Report dated Dec. 2, 2014, in PCT/JP2014/075945 filed Sep. 29, 2014.
(Continued)

*Primary Examiner* — Jerome Grant, II
(74) *Attorney, Agent, or Firm* — Oblon, McClelland, Maier & Neustadt, L.L.P.

(57) ABSTRACT

An image analyzing apparatus, a non-transitory computer readable medium storing a program, and a method are provided for extracting voids from a three-dimensional image of a fiber-reinforced composite material. The image analyzing apparatus includes a processor which executes image processing to the three-dimensional image. The processor binarizes the three-dimensional image and creates a binary image, transforms the binary image into a distance and creates a distance image, executes closing processing to the binary image by using the distance image, extracts voids from differences between images before and after the clos-
(Continued)

ing processing, among the extracted voids, classifies voids that are adjacent to a background voxel as open voids, and classifies voids that are not adjacent to a background voxel as closed voids, and executes opening processing to the open voids in order to eliminate fake voids.

8 Claims, 6 Drawing Sheets

(51) Int. Cl.
| | | |
|---|---|---|
| G01N 23/04 | (2006.01) | |
| G01N 21/88 | (2006.01) | |
| G06K 9/52 | (2006.01) | |
| G06K 9/62 | (2006.01) | |
| G06T 1/20 | (2006.01) | |
| G06T 7/60 | (2017.01) | |

(52) U.S. Cl.
CPC ............. *G06K 9/52* (2013.01); *G06K 9/6215* (2013.01); *G06K 9/6267* (2013.01); *G06T 1/20* (2013.01); *G06T 7/0006* (2013.01); *G06T 7/60* (2013.01); *G01N 2021/8887* (2013.01); *G01N 2223/615* (2013.01); *G06T 2200/04* (2013.01); *G06T 2207/10028* (2013.01); *G06T 2207/10081* (2013.01); *G06T 2207/20036* (2013.01); *G06T 2207/30108* (2013.01); *G06T 2207/30164* (2013.01)

(56) References Cited

U.S. PATENT DOCUMENTS

| | | | |
|---|---|---|---|
| 2013/0155061 A1* | 6/2013 | Jahanshahi | G06T 15/00 345/419 |
| 2014/0031967 A1* | 1/2014 | Unger | B29C 67/0088 700/119 |
| 2015/0233840 A1* | 8/2015 | Amanullah | G01N 21/8806 348/46 |
| 2016/0181061 A1* | 6/2016 | Kim | H01J 37/222 250/307 |
| 2016/0198951 A1* | 7/2016 | Fujino | A61B 3/1005 351/206 |

OTHER PUBLICATIONS

Ando, "X Sen CT no Genri to Katsuyo," Idemitsu Technical Report, vol. 52, No. 2, Jun. 2009 (with English translation, 11 pages).
Extended European Search Report dated Apr. 12, 2017 in Patent Application No. 14847556.9.
E. Weber, et al., "Comparison of X-Ray Micro-Tomography Measurements of Densities and Porosity Principally to Values Measured by Mercury Porosimetry for Carbon-Carbon Composites" ScienceDirect, Carbon, vol. 48, XP 26996063, Jul. 1, 2010, pp. 2151-2158.
M. Kosek, et al., "Visualization of Voids in Actual C/C Woven Composite Structure", Composites Science and Technology, vol. 69, XP 26128586, Jul. 1, 2009, pp. 1465-1469.

* cited by examiner

IMAGE ANALYZING APPARATUS AND PROGRAM

TECHNICAL FIELD

The present disclosure relates to an image analyzing apparatus and program, and in particular can be suitably applied to an image analyzing apparatus and program capable of extracting the voids contained in a fiber-reinforced composite material.

BACKGROUND ART

In recent years, the development of ceramic matrix composites (CMC) as one type of fiber-reinforced composite material is being promoted. CMC is a composite material in which ceramic fiber is reinforced with a matrix, and is characterized in being light and having superior heat resistance properties. By leveraging these characteristics, for instance, the possibility of using CMC in aircraft engine parts is being considered, and the practical application thereof is currently being sought. Note that the use of CMC as aircraft engine parts is expected to considerably improve the fuel economy.

The general process of forming CMC is as follows. Foremost, roughly several hundred ceramic fibers are bundled to prepare a fiber bundle, and the prepared fiber bundles are woven into a fabric. As the weaving method of fiber bundles, for instance, known are methods referred to as three-dimensional weaving and plain weaving. Three-dimensional weaving is a method of weaving the fiber bundles from three directions (XYZ directions) to prepare a fabric, and plain weaving is a method of weaving the fiber bundles from two directions (XY directions) to prepare a fabric.

After the fabric is prepared, a matrix is formed in the voids in the fiber bundles and between the fiber bundles via matrix forming processes known as CVI (Chemical Vapor Infiltration) and PIP (Polymer Impregnation and Pyrolysis). The CMC is thereafter formed by ultimately performing machining and surface coating.

Here, while CVI and PIP in the formation process of CMC are processes for forming a matrix in the voids, in effect it is difficult to form a matrix for filling all voids. Thus, a matrix is not formed and voids will remain on the surface and inside the formed CMC. The distribution of these remaining voids will considerably affect the strength of the CMC.

For example, in cases where numerous voids exist in a local area, the strength of that local area will deteriorate considerably. Thus, in order to confirm whether the strength of the formed CMC is constant or sufficient, it is important to appropriately evaluate the void distribution. In other words, it is important to accurately extract the voids.

PTL 1 discloses a technique of creating a void extraction image from an X-ray transfer image of an engine skirt. Specifically, morphology processing is executed to the X-ray transfer image of the engine skirt for eliminating noise, binarization processing is executed to the image that underwent the morphology processing, and a circular foreground in the image that underwent the binarization processing is determined to be a void and extracted. Meanwhile, with regard to an oval foreground in the image that underwent the binarization processing, a circular foreground within the oval shape is extracted by once again executing binarization processing upon changing the threshold, and this is determined to be a void and extracted. Finally, a void extraction image is created by synthesizing the plurality of circular voids that were extracted.

CITATION LIST

Patent Literature

[PTL 1] Japanese Patent Application Publication No. 2009-198463

SUMMARY

Technical Problem

Nevertheless, the technology described in PTL 1 does not give any consideration to a three-dimensional image. Thus, when an attempt is made to simply apply the technology described in PTL 1 to a three-dimensional image, there is a problem in that a huge amount of calculation time will become required. For example, with the technology described in PTL 1, while morphology processing is foremost executed to the X-ray transfer image upon extracting the voids, when this morphology processing is executed to a three-dimensional image, calculation time is required for an amount obtained by multiplying the cube of the radius of the sphere in cases where the structural element is a sphere and the number of surface pixels of the target image.

Moreover, while the technology described in PTL 1 is able to extract circular voids, it is unable to extract voids of other shapes. The voids in the CMC are formed on the surface and inside the CMC during the foregoing formation process, and, while certain voids existing internally may be circular, the shape of all voids is not necessarily circular. Moreover, since the voids existing on the surface are adjacent to the background, they are not of a specific closed shape. Thus, with the technology described in PTL 1, it is not possible to accurately extract the voids existing on the surface and inside the CMC.

The present disclosure was devised in view of the foregoing problems, and proposes an imaging analyzing apparatus and program in which voids can be extracted from a three-dimensional image of CMC in a short time and accurate manner.

Solution to Problem

In order to achieve the foregoing object, the present disclosure provides an image analyzing apparatus for extracting voids from a three-dimensional image of a fiber-reinforced composite material, wherein the image analyzing apparatus comprises a processor which executes image processing to the three-dimensional image, and the processor binarizes the three-dimensional image and creates a binary image, transforms the binary image into a distance and creates a distance image, executes closing processing to the binary image by using the distance image, extracts voids from differences between images before and after the closing processing, among the extracted voids, classifies voids that are adjacent to a background voxel as open voids, and classifies voids that are not adjacent to a background voxel as closed voids, and executes opening processing to the open voids in order to eliminate fake voids.

Moreover, in order to achieve the foregoing object, the present invention provides a program for extracting voids from a three-dimensional image of a fiber-reinforced composite material, wherein the program causes a computer to execute a first step of binarizing the three-dimensional image and creating a binary image, a second step of transforming the binary image into a distance and creating a distance image, a third step of executing closing processing to the binary image by using the distance image, a fourth step of extracting voids from differences between images before and after the closing processing, a fifth step of, among the extracted voids, classifying voids that are adjacent to a background voxel as open voids, and classifying voids that are not adjacent to a background voxel as closed voids, and a sixth step of executing opening processing to the open voids in order to eliminate fake voids.

Effects

According to the present disclosure, voids can be extracted from a three-dimensional image of CMC in a short time and accurate manner.

DESCRIPTION OF EMBODIMENTS

Figure 1:
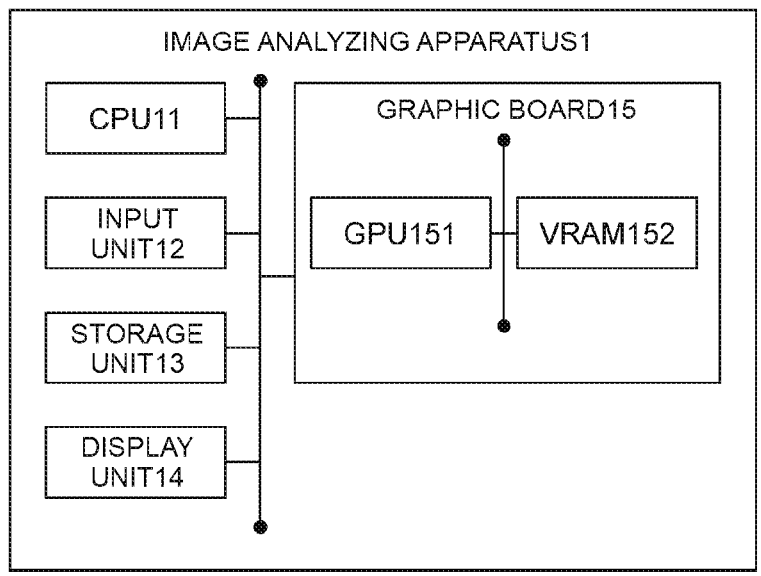
FIG. 1 is an overall configuration diagram of the image analyzing apparatus in this embodiment.

An embodiment of the present disclosure is now explained in detail with reference to the drawings.
(1) Overall Configuration FIG. 1 shows the overall configuration of the image analyzing apparatus 1 in this embodiment. The image analyzing apparatus 1 is a computer configured by comprising a CPU (Central Processing Unit) 11, an input unit 12, a storage unit 13, a display unit 14 and a graphic board 15.

The CPU 11 is a processor that coordinates with the various programs stored in the CPU 11 or coordinates with the GPU 151 described later and controls the operation of the image analyzing apparatus 1. The input unit 12 is an interface for receiving inputs from a user and is configured, for example, from a keyboard or a mouse. Moreover, the input device 12 in this embodiment is also an interface for inputting a CT image that is obtained by imaging the CMC (Ceramic Matrix Composites) with an X-ray CT device.

CMC refers to a fiber-reinforced composite material that is formed by bundling roughly several hundred ceramic fibers to prepare a fiber bundle, weaving the prepared fiber bundles into a fabric, thereafter coating the fiber surface with carbon or the like, forming a matrix in the voids in the fiber bundles and between the fiber bundles based on a matrix forming process referred to as CVI (Chemical Vapor Infiltration) and PIP (Polymer Impregnation and Pyrolysis), and finally performing machining, surface coating and other processes.

While CVI and PIP in the formation process of CMC are processes for forming a matrix in the voids, in effect it is difficult to form a matrix for filling all voids. Thus, a matrix is not formed and voids will remain on the surface and inside the formed CMC. The distribution of these remaining voids will considerably affect the strength of the CMC.

This embodiment attempts to extract the voids existing on the surface and inside the CMC in a short period and accurate manner from a CT image (three-dimensional image) that is obtained by imaging the CMC using an X-ray CT device. Since the image analyzing apparatus 1 in this embodiment realizes the shortening of the calculation time required for extracting the voids, and realizes the improvement of the extraction accuracy, it can be effectively used in product inspection.

Returning to FIG. 1, the storage unit 13 is a storage medium for storing the CT image input from the input unit 12 and the images that are created by processing and correcting the obtained CT image through various types of image processing. The display unit 14 is a display device such as an LCD (Liquid Crystal Display) for displaying the CT image and the images that are created by processing and correcting the CT image through various types of image processing.

The graphic board 15 is configured by comprising a GPU (Graphics Processing Unit) 151 and a VRAM (Video RAM) 152 which can be accessed by the GPU 151 at high speed. The GPU 151 is a processor that mainly handles image processing, and several hundred processors are integrated in a single GPU 151.

Figure 2:
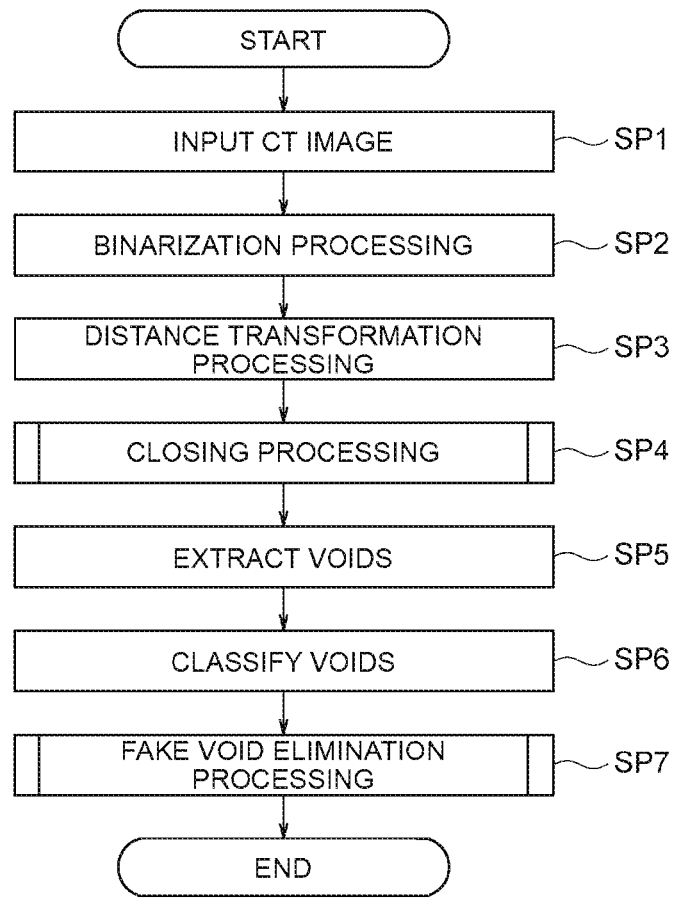
FIG. 2 is a flowchart showing the void extraction processing.

The GPU 151 can process images, without burdening the CPU 11, by executing image processing based on various programs (referred to as kernel programs) that are loaded from the CPU 11, and draw the processed images on the display unit 14 at high speed. A computer such as the image analyzing apparatus 1 which enables the CPU 151 on the graphic board 15 to perform high-speed image processing is specifically referred to as a GPGPU (General Purpose Graphics Processing Unit). Details of the image processing executed by the GPU 151 will be described later (FIG. 2 to FIG. 8).
(2) Overall Processing FIG. 2 shows the processing routine of the void extraction processing in this embodiment. This void extraction processing is started when the input unit 12 receives an execution instruction from a user, and is executed through coordination of the GPU 151 and the kernel program loaded in the GPU 151. In the ensuing explanation, the GPU 151 is explained as the processing subject for the sake of convenience of explanation.

Foremost, when the GPU 151 inputs a CT image via the input unit 12 (SP1), the GPU 151 executes binarization processing to the input CT image (SP2). Subsequently, the GPU 151 executes distance transformation processing to the image (binary image) that underwent the binarization processing (SP3).

In the distance transformation processing, for instance, Dijkstra's algorithm or the wavefront method is used. Dijkstra's algorithm is a method where, when the background voxels adjacent to the foreground are used as the boundary voxels, the distance to all such boundary voxels is calculated with regard to the respective foreground voxels, and the minimum value is calculated among the calculation results. The minimum value becomes the distance value of that foreground voxel. When the number of foreground voxels is N and the number of boundary voxels is M, the calculation time will be N×M.

The wavefront method is a method of searching for the boundary voxel in which the distance will be minimal among all boundary voxels regarding the respective foreground voxels, and calculating the distance to the boundary voxel that was obtained as the search result. While the obtained distance value will be the same with the Dijkstra's algorithm and the wavefront method even through the algorithm is different, when the number M of boundary voxels is great, the calculation time can be shortened by using the wavefront method. The calculation time required for the distance transformation processing when using the wavefront method will be N log N.

Figure 3:
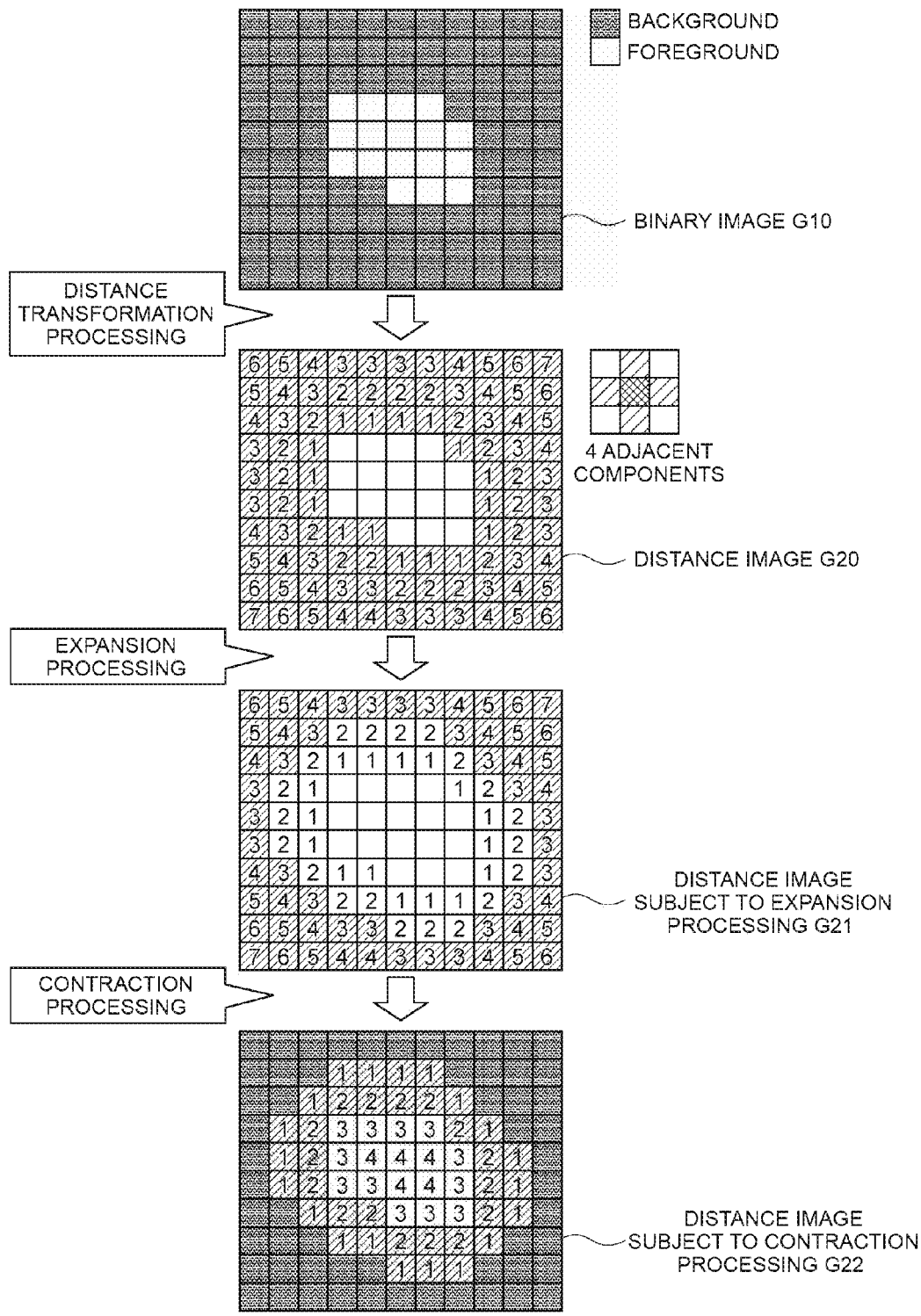
FIG. 3 is a conceptual diagram of the distance transformation processing.
Figure 4:
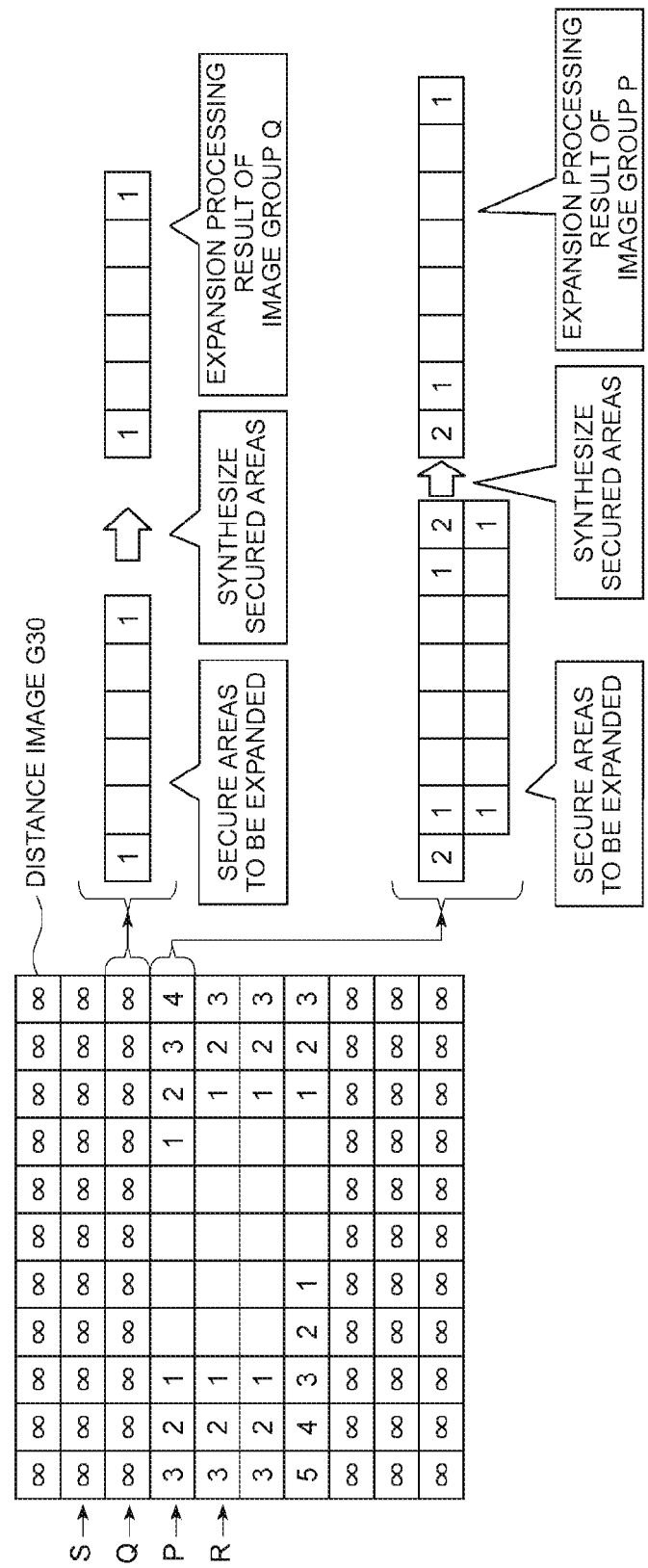
FIG. 4 is a conceptual diagram of the expansion processing using a distance image.

The image (distance image) that underwent the distance transformation processing is once stored in the memory of the GPU 151 or the VRAM 152. The distance stored in the memory or the VRAM 152 is used for shortening the calculation time in the closing processing described later. The distance transformation processing and the method of using the distance image will be described later (FIG. 3 and FIG. 4).

Next, the GPU 151 executes closing processing for extracting the voids (SP4). Closing processing is one type of morphology processing, and is processing of executing expansion processing to the target image by using a structural element of a predetermined shape (sphere in this embodiment), and thereafter performing contraction processing to the image that underwent expansion processing by using the same structural element.

Figure 5:
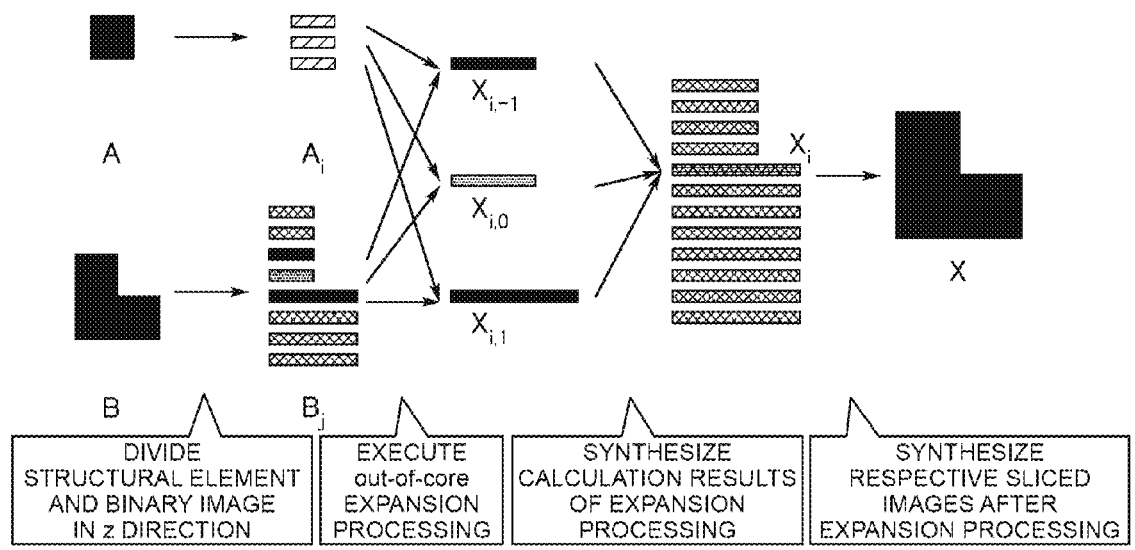
FIG. 5 is a conceptual diagram of the closing processing.
Figure 6:
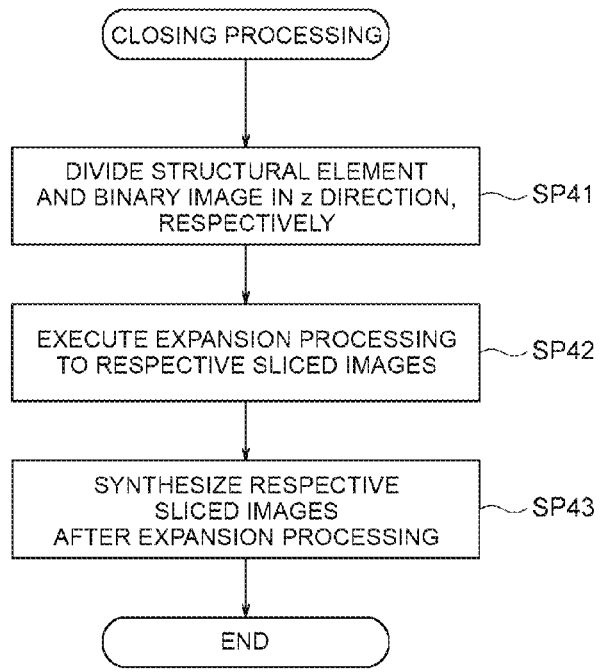
FIG. 6 is a flowchart showing the details of the closing processing.

With the image that underwent expansion processing, it can be assumed that the voids have been filled with the structural element. Thus, the voids can be extracted by subtracting the binary image containing voids before undergoing the closing processing, from the binary image that underwent the closing processing in which the voids have been filled. Details regarding the closing processing of this embodiment will be described later (FIG. 5 and FIG. 6).

Thus, the GPU 151 extracts the voids by calculating the difference between the binary image that underwent the closing processing in which the voids have been filled, and the binary image containing the voids before undergoing the closing processing (SP5). The voids that are extracted here are both the voids (open voids) which are adjacent to the background voxel and the voids (closed voids) which are not adjacent to the background voxel.

The closed voids are the voids that exist inside the CMC, and exist as independent background voxels in the binary image. Thus, for instance, these can be easily extracted by executing the well-known connected component labeling processing. Meanwhile, the open voids are the voids that exist on the surface of the CMC, and the boundary with the background is unclear in the binary image. Thus, it is difficult to extract the open voids.

When a large structural element is used, locations that are not voids may be falsely recognized as voids. Meanwhile, when a small structural element is used, due to the fundamental rule of the morphology processing of not recognizing large voids, among the voids extracted in step SP5, locations that are not voids may be extracted as voids. In other words, among the extracted voids, there is a possibility that certain open voids will be falsely recognized as voids.

Thus, in order to eliminate the voids (fake voids) among the open voids which are a background and not actually voids, the GPU 151 foremost classifies the voids extracted in step SP5 into open voids and closed voids (SP6).

Figure 7:
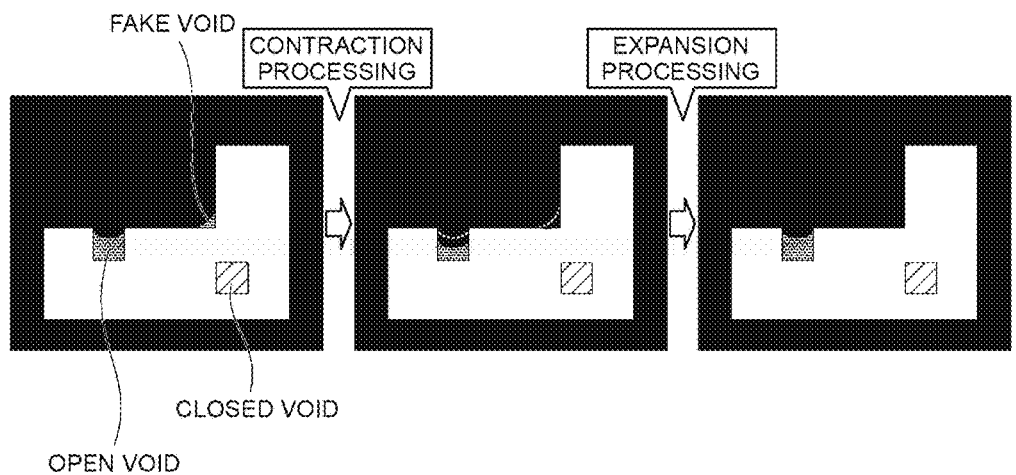
FIG. 7 is a conceptual diagram of the fake void elimination processing.
Figure 8:
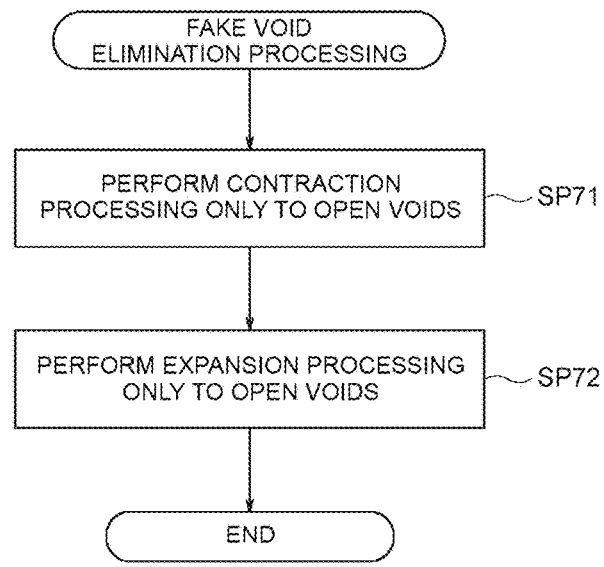
FIG. 8 is a flowchart showing the details of the fake void elimination processing.

Next, the GPU 151 executes fake void elimination processing for eliminating the fake voids from the voids that were classified as being open voids (SP7). The voids can be accurately extracted by eliminating the fake voids in step SP7. Details regarding the fake void elimination processing in this embodiment will be described later (FIG. 7 and FIG. 8).

After executing the respective processes of step SP1 to SP7 described above, the GPU 11 ends the void extraction processing.

(3) Details of Processing

Details of the respective processes (SP3, SP4, SP7) explained in FIG. 2 are now explained with reference to FIG. 3 to FIG. 8 and based on calculation formulas (Formula 1 to Formula 5). Explanation of the CT image input processing (SP1), the binarization processing (SP2), the void extraction processing (SP5) and the classification processing (SP6) is omitted since they are based on general methods or well-known methods.

FIG. 3 shows a standard conceptual diagram of the distance transformation processing. When distance transformation processing is executed to the binary image G10 by using four adjacent components, the distance image G20 is created. Note that the adjacent pixels in the case of using four adjacent components will be the pixels positioned above and below and at the left and right of the target pixels.

On the background pixels in the distance image G20, shown is the distance value in which the distance will be the shortest as the calculation result when the distance from the respective surface pixels of the foreground to the target background pixels is calculated using the four adjacent components. To put it differently, the shortest distance from the target background pixels to the foreground surface pixels is shown on the background pixels in the distance image G20. While the distance value shown here is the distance value in the case of using the four adjacent components in order to simplify the explanation, in effect the Euclidean distance is calculated. The Euclidean distance is, for example, when there are the two points of A and B in a two-dimensional image and the coordinates of the respective points are (x1, y1), (x2, y2), the distance between the two points of A and B that is calculated based on $$\sqrt{((x1-x2)^2+(y1-y2)^2)}.$$

When expansion processing is executed to this distance image G20 within a range where the distance value is 2, the distance image G21 is created. Moreover, when contraction processing is executed to distance image G21 within a range where the distance value is 2, the distance image G22 is created. Note that, on the foreground pixels in the distance image G222, shown is the distance value in which the distance will be the shortest as the calculation result when the distance from the respective surface pixels of the background to the foreground pixels is calculated using the four adjacent components.

In this embodiment, the calculation time required for the closing processing can be shortened by using these distance images in the closing processing. In other words, if the distance from the foreground is calculated in advance, the respective sliced images obtained by dividing the three-dimensional image can be expanded or contracted based on a prescribed distance value. Furthermore, by calculating the sum set of the respective sliced images that were expanded or contracted, the same image as the image that is obtained by subjecting the three-dimensional image to closing processing can be obtained.

FIG. 4 shows a conceptual diagram of the out-of-core expansion processing using distance images. Here, explained are the expansion processing when the pixel group P in the 4th line from the top in the distance image G30 is used as the target pixel group, and the expansion processing when the pixel group Q in the 3rd line from the top in the distance image G30 is used as the target pixel group. Moreover, explained is a case of expanding the structural element (circular in this example) having a radius of 2 in each of the foregoing cases.

Foremost, to explain the expansion processing of the pixel group P, when a circle having a radius of 2 is moved above the pixel group P, the background pixels having a distance value of 2 or less will become the area of expansion regarding the pixel group P, and the background pixels having a distance value of √3 or less will become the area of expansion regarding the pixel groups Q and R. Accordingly, expansion processing is executed to the pixel group P by expanding each of the pixel groups P, Q, R, which are in the area to be expanded, based on a prescribed distance value, and thereafter synthesizing each of the expanded areas.

In effect, with regard to the pixel group P, the background pixels having a distance value of 1 and 2 are secured as the area for expansion. Moreover, with regard to the pixel group R, the background pixels having a distance value of 1 are secured as the area for expansion, and with regard to the pixel group Q, an area for expansion is not secured since the distance value is ∞. And by synthesizing the areas that were respectively secured for the pixel groups P, Q, R (here, based on the areas that were secured for the pixel groups P and R), the expansion processing result of the pixel group P can be obtained.

The expansion processing of the pixel group Q is now explained. When a circle having a radius of 2 is moved above the pixel group Q, the background pixels having a distance value of 2 or less will become the area of expansion regarding the pixel group P, and the background pixels having a distance value of √3 or less will become the area of expansion regarding the pixel groups P and S. Accordingly, expansion processing is executed to the pixel group Q by expanding each of the pixel groups Q, P and S, which are in the area to be expanded, based on a prescribed distance value, and thereafter synthesizing each of the expanded areas.

In effect, with regard to the pixel groups Q and S, an area for expansion is not secured since the distance value is ∞, and with regard to the pixel group P, the background pixels having a distance value of 1 are secured as the area of expansion. And by synthesizing the areas that were respectively secured for the pixel groups Q, P and S (here, only based on the area that was secured for the pixel group P), the expansion processing result of the pixel group Q can be obtained. Even in case where the distance value of the pixel group Q is not properly calculated, an appropriate expansion processing result can be obtained regarding the pixel group Q.

FIG. 5 shows a conceptual diagram of the closing processing (SP4). By way of reference, the expansion processing in the closing processing can be represented with Formula 1 below when the structural element is A and the image is B.

[Math 1]

$$A \oplus B = \cup_{b \in B} A(b) \tag{1}$$

A(b): Parallel translation of A based on vector b

When the GPU 151 attempts to simply perform this expansion processing, not only is it necessary to store all images B in the memory of the GPU 151, it is also necessary to secure the storage area of the calculation result. Thus, when the image B is a three-dimensional image as in this embodiment, depending on the performance of the image analyzing apparatus 1, it may be difficult for the GPU 151 to perform the processing of Formula 1 above as is.

Thus, considered is a case of dividing the structural element A and the image B each in the z direction, executing expansion processing in parallel to the subsets $A_i$ and $B_j$, and thereafter calculating the sum set of the calculation result. The subsets $A_i$ and $B_j$ are shown in Formula 2 and Formula 3 below.

[Math 2]

$$A = \cup_i A_i(0) \tag{2}$$

$$B = \cup_j B_j \tag{3}$$

Moreover, based on Formula 1 to Formula 3 above, the expansion processing will be as represented in Formula 4 below.

[Math 3]

$$A \oplus B = \cup_i A_i(0) \oplus \cup_j B_j = \cup_i \cup_j \{A_i(0) \oplus B_j\} \tag{4}$$

Based on Formula 4 above, the expansion processing of a three-dimensional image can obtain the same results as Formula 1 above, which simply executed the expansion processing of the overall three-dimensional image, by executing the expansion processing to the respective sliced images, and thereafter calculating the sum set of the respective sliced images that underwent the expansion processing. In other words, the expansion processing of a three-dimensional image can be treated as the expansion processing of a two-dimensional image.

Note that the structural element A in this embodiment is a sphere, and when the radius of the structural element A is r and the distance between the fiber bundles is d, the radius r of the structural element A will be as represented in Formula 5 below in light of the fact that the fiber bundles configuring the CMC will be regularly arranged.

[Math 4]

$$r \leq \frac{d}{2} \tag{5}$$

In FIG. 5, the structural element A is configured from the subset $A_i$ which is divided into three in the z direction, the image B is configured from the subset $B_j$ which is divided into eight in the z direction. Moreover, FIG. 5 shows a case of performing out-of-core expansion processing, and shows a case of processing of the subset A expanding the middle level of the subset $B_j$ (fourth sliced image from the top). The fact that distance images are used in the out-of-core expansion processing is as explained in FIG. 4.

Since the range that the subset A influences the expansion of the middle level of the subset $B_j$ is i=−1, 0, 1 in this example, the expansion processing of $X_{i,-1}$, $X_{i,0}$, $X_{i,1}$ is calculated using the distance image, and the result $X_i$ of the expansion processing of the middle level of the subset $B_j$ is obtained by synthesizing the foregoing results. As a result of similarly synthesizing the results of the expansion processing for all sliced images, the three-dimensional image X that underwent the expansion processing can be obtained.

Note that the contraction processing can be calculated in the same manner as the foregoing expansion processing since it can be represented as $(A+B^C)^C$ by using the complementary set $B^C$ of the image B. By combining the expansion processing and the contraction processing, high-speed closing processing can be realized. According to the closing processing of this embodiment, the memory capacity required in the GPU 151 is for roughly two cross section images, and the GPU 151 can execute the closing processing even for mass data.

FIG. 6 shows the detailed processing routine of the closing processing (SP4). As explained with reference to FIG. 5, the GPU 151 foremost divides the structural element and the binary image each in the z direction (SP41). Next, the GPU 151 executes expansion processing to the respective sliced images (SP42). Finally, the GPU 151 synthesizes the respective sliced images that underwent expansion processing (SP43), and then ends the closing processing.

FIG. 7 shows a conceptual diagram of the fake void elimination processing (SP7). A fake void is a void in which a part of the background that is falsely recognized as an open void among the open voids classified in step SP6. Since a fake void is actually smaller than an open voids and has a minute shape, the GPU 151 executes the opening processing as a method of eliminating these minute foreground components.

Opening processing is one type of morphology processing, and is processing of executing contraction processing to the target image by using a structural element of a predetermined shape (sphere in this embodiment), and thereafter performing expansion processing to the image that underwent contraction processing by using the same structural element. Note that, here, the opening processing is executed only to the open voids.

Accordingly, in FIG. 7, contraction processing is foremost executed only to the open voids by using a structural element having a prescribed radius. Note that, here, the structural element that is used is a sphere having a radius that is not greater than the radius of the fiber bundle. As a result, all fake voids are replaced with background voxels and will disappear, and the actual open voids are replaced with background voxels as a result of their surfaces being ground in the amount of the radius of the structural element, but will continue to remain.

Next, expansion processing is executed only to the open voids that underwent the contraction processing by using the same structural element. As a result, the fake voids that disappeared will continue to be replaced with the background voxels without reappearing, and the surface of the actual open voids will reappear in the amount of the radius of the structural element.

FIG. 8 shows the detailed processing routine of the fake void elimination processing (SP7). As explained with reference to FIG. 7, the GPU 151 foremost executes contraction processing to the open voids (SP71). Next, the GPU 151 executes expansion processing only to the open voids that underwent contraction processing (SP72), and then ends the fake void elimination processing.

(4) Images

Figure 9:
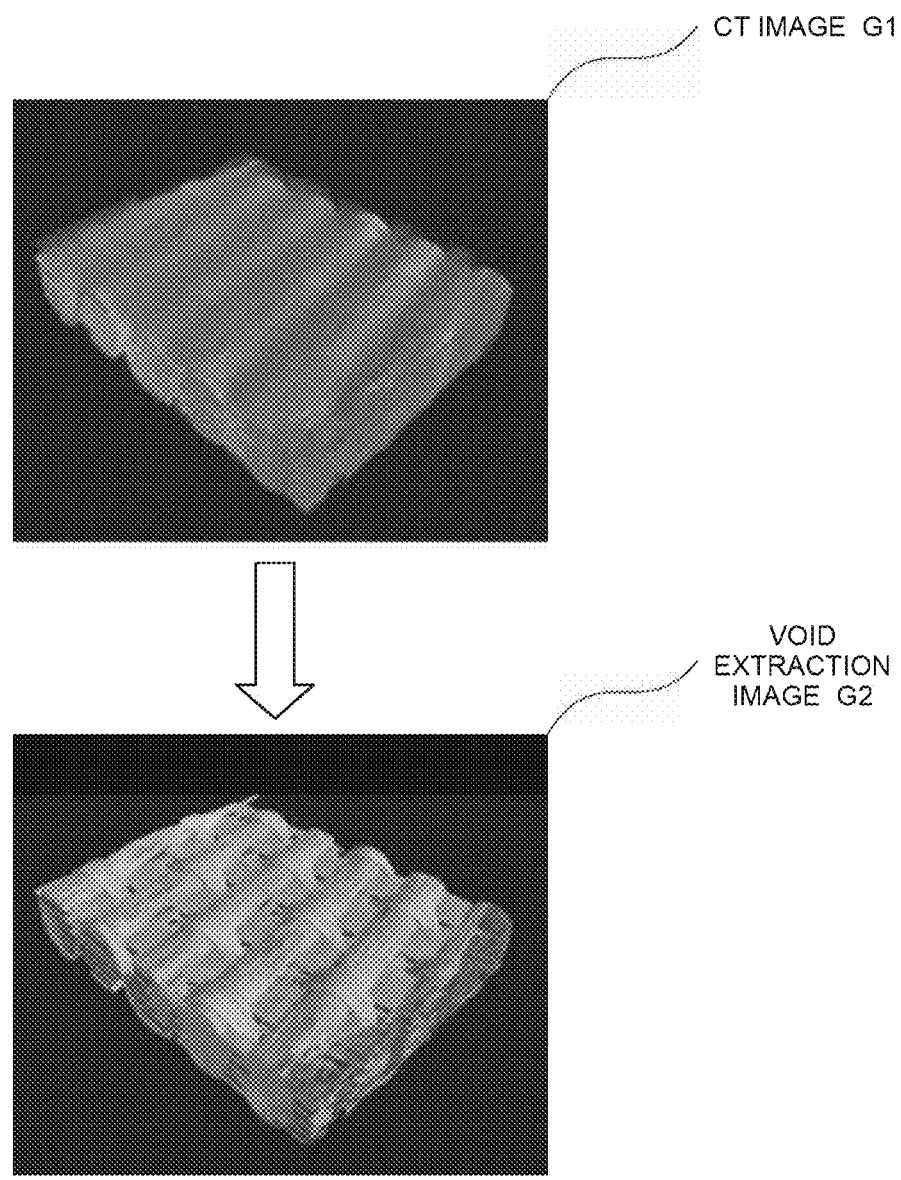
FIG. 9 is a diagram showing a specific example of the image obtained from the void extraction processing.

FIG. 9 shows a specific example of the images that are actually obtained as a result of executing the void extraction processing (SP1 to SP7) described above. The CT image G1 is the three-dimensional image that is obtained by imaging the CMC, which is configured from fabric produced via three-dimensional weaving, using an X-ray CT device. The CT image G1 is input into the image analyzing apparatus 1 via the input unit 12.

Moreover, the void extraction image G2 is a three-dimensional image that is obtained as a result of executing the void extraction processing (FIG. 2) to the input CT image G1. The void extraction image G2 is displayed in a manner which enables the differentiation of closed voids and open voids.

(5) Effects of this Embodiment

According to the image analyzing apparatus and program in this embodiment described above, since binarization processing is executed to a three-dimensional image of the CMC, and distance transformation processing is executed to the binary image and closing processing is executed by using the results of the distance transformation processing, it is possible to shorten the calculation time required for extracting the voids. Moreover, among the extracted voids, since opening processing is executed to eliminate the fake voids regarding the open voids, it is possible to accurately extract the voids. Thus, voids can be extracted from a three-dimensional image of the CMC in a short time and accurate manner.

REFERENCE SIGNS LIST

1 Image analyzing apparatus
11 CPU
12 Input unit
13 Storage unit
14 Display unit
15 Graphic board
151 GPU
152 VRAM

The invention claimed is:

1. An image analyzing apparatus for extracting voids from a three-dimensional image of a fiber-reinforced composite material, the image analyzing apparatus comprising:
   a processor which executes image processing to the three-dimensional image, wherein the processor:
   binarizes the three-dimensional image and creates a binary image;
   transforms the binary image into a distance and creates a distance image;
   executes closing processing to the binary image by using the distance image;
   extracts voids from differences between images before and after the closing processing;
   among the extracted voids, classifies voids that are adjacent to a background voxel as open voids, and classifies voids that are not adjacent to a background voxel as closed voids;
   executes opening processing to the open voids in order to eliminate fake voids; and
   in the closing processing:
   executes expansion processing to the binary image by dividing the binary image into a plurality of two-dimensional images, expanding each of the plurality of two-dimensional images by using the distance image corresponding to each of the plurality of two-dimensional images, and calculating a sum set of the plurality of two-dimensional images that were expanded, and
   executes contraction processing to the binary image that underwent the expansion processing by dividing the binary image that underwent the expansion processing into a plurality of two-dimensional images, contracting each of the plurality of two-dimensional images by using the distance image corresponding to each of the plurality of two-dimensional images that were divided, and calculating a sum set of the plurality of two-dimensional images that were contracted.

2. The image analyzing apparatus according to claim 1, wherein the processor, in the closing processing:

expands or contracts each of the plurality of two-dimensional images by using, as a structural element, a sphere having a radius of a value that is half or less of the distance between the fiber bundles configuring the fiber-reinforced composite material.

3. The image analyzing apparatus according to claim 1, wherein the processor, in the opening processing:
executes contraction processing and expansion processing only to the open voids.

4. The image analyzing apparatus according to claim 3, wherein the processor, in the opening processing:
executes the contraction processing and the expansion processing by using, as a structural element, a sphere having a radius of a value that is half or less of the radius of the fiber bundles configuring the fiber-reinforced composite material.

5. The image analyzing apparatus according to claim 1, wherein the processor is a GPU which executes image processing to the three-dimensional image based on a kernel program loaded from a CPU.

6. The image analyzing apparatus according to claim 1, wherein the three-dimensional image of the fiber-reinforced composite material is an image obtained by imaging the fiber-reinforced composite material, which is configured from fabrics produced via three-dimensional weaving or plain weaving, using an X-ray CT device.

7. A non-transitory computer readable medium storing a program for extracting voids from a three-dimensional image of a fiber-reinforced composite material, wherein the program causes a computer to execute a method comprising:
binarizing the three-dimensional image and creating a binary image;
transforming the binary image into a distance and creating a distance image;
executing closing processing to the binary image by using the distance image;
extracting voids from differences between images before and after the closing processing;
among the extracted voids, classifying voids that are adjacent to a background voxel as open voids, and classifying voids that are not adjacent to a background voxel as closed voids;
executing opening processing to the open voids in order to eliminate fake voids; and
in the closing processing:
executing expansion processing to the binary image by dividing the binary image into a plurality of two-dimensional images, expanding each of the plurality of two-dimensional images by using the distance image corresponding to each of the plurality of two-dimensional images, and calculating a sum set of the plurality of two-dimensional images that were expanded, and
executing contraction processing to the binary image that underwent the expansion processing by dividing the binary image that underwent the expansion processing into a plurality of two-dimensional images, contracting each of the plurality of two-dimensional images by using the distance image corresponding to each of the plurality of two-dimensional images that were divided, and calculating a sum set of the plurality of two-dimensional images that were contracted.

8. A method for extracting voids from a three-dimensional image of a fiber-reinforced composite material, the method comprising:
binarizing the three-dimensional image and creating a binary image;
transforming the binary image into a distance and creating a distance image;
executing closing processing to the binary image by using the distance image;
extracting voids from differences between images before and after the closing processing;
among the extracted voids, classifying voids that are adjacent to a background voxel as open voids, and classifying voids that are not adjacent to a background voxel as closed voids;
executing opening processing to the open voids in order to eliminate fake voids; and
in the closing processing:
executing expansion processing to the binary image by dividing the binary image into a plurality of two-dimensional images, expanding each of the plurality of two-dimensional images by using the distance image corresponding to each of the plurality of two-dimensional images, and calculating a sum set of the plurality of two-dimensional images that were expanded, and
executing contraction processing to the binary image that underwent the expansion processing by dividing the binary image that underwent the expansion processing into a plurality of two-dimensional images, contracting each of the plurality of two-dimensional images by using the distance image corresponding to each of the plurality of two-dimensional images that were divided, and calculating a sum set of the plurality of two-dimensional images that were contracted.

* * * * *